US008609814B2

(12) United States Patent
Cooper et al.

(10) Patent No.: US 8,609,814 B2
(45) Date of Patent: Dec. 17, 2013

(54) MODIFIED GLOBIN PROTEINS WITH ALTERED ELECTRON TRANSPORT PATHWAY

(75) Inventors: Christopher Eric Cooper, Colchester (GB); Michael Thomas Wilson, Colchester (GB); Brandon Jon Reeder, Colchester (GB)

(73) Assignee: University of Essex Enterprises Limited, Essex (GB)

( * ) Notice: Subject to any disclaimer, the term of this patent is extended or adjusted under 35 U.S.C. 154(b) by 646 days.

(21) Appl. No.: 12/452,075

(22) PCT Filed: Jun. 26, 2008

(86) PCT No.: PCT/GB2008/002199
§ 371 (c)(1),
(2), (4) Date: Dec. 15, 2009

(87) PCT Pub. No.: WO2009/004309
PCT Pub. Date: Jan. 8, 2009

(65) Prior Publication Data
US 2010/0137189 A1 Jun. 3, 2010

(30) Foreign Application Priority Data

Jun. 29, 2007 (GB) .................................. 0712685.7

(51) Int. Cl.
*A61K 35/14* (2006.01)
(52) U.S. Cl.
USPC ........... 530/385; 530/380; 530/400; 514/13.4
(58) Field of Classification Search
USPC .......................... 530/385, 380, 400; 514/13.4
See application file for complete search history.

(56) References Cited

U.S. PATENT DOCUMENTS 5,028,588 A 7/1991 Hoffman et al.

FOREIGN PATENT DOCUMENTS

| WO | 88/09179 | 12/1988 |
| WO | 97/15591 | 5/1997 |
| WO | WO 2009/004310 A1 | 1/2009 |

OTHER PUBLICATIONS

Weiland (J. Am. Chem. Soc. 126(38), 11930-11935, 2004).*
Huth, S. W. (J. Am. Chem. Soc. 98(26), 8467-8471, 1976).*
Juckett (Biophysical Chemistry 19(4), 321-335, 1984).*
Alayash (Archives of Biochemistry and Biophysics 303(2), 332-338, 1993).*
Jorgensen, Free radical research, (Jul. 1997) vol. 27, No. 1, pp. 73-87.*
Burkert (Blood 48, 645-651, 1976).*
Abstract of Baudin, V., Transfusion Clinique et Biologique 2(6) 463-467, 1995.*
Vollaard et al, "A new sensitive assay reveals that hemoglobin is oxidatively modified in vivo", Free Radical Biology & Medicine 39 (2005) 1216-1228.
Reeder et al, "Hemoglobin and Myoglobin Associated Oxidative Stress: from Molecular Mechanisms to Disease States", Current Medicinal Chemistry, 2005, 12, 2741-2751.
Reeder et al, "Desferrioxamine Inhibits Production of Cytotoxic Heme to Protein Cross-Linked Myoglobin: A Mechanism to Protect against Oxidative Stress without Iron Chelation", Chem. Res. Toxicol. 2005, 18, 1004-1011.
Cooper et al, "On the formation, nature, stability and biological relevance of the primary reaction intermediates of myoglobins with hydrogen peroxide", Dalton Trans., 2005, 3483-3488.
Davies et al, "Nitrosyl heme production compared in endotoxemic and hemorrhagic shock", Free Radical Biology & Medicine 38 (2005) 41-49.
Silaghi-Dumitrescu et al, "Transient species involved in catalytic dioxygen/peroxide activation by hemoproteins: possible involvement of protonated Compound I species", Dalton Trans., 2005, 3477-3482.
Dunne et al, "Ascorbate removes key precursors to oxidative damage by cell-free haemoglobin in vitro and in vivo", Biochem J. (2006) 399, 513-524.
Cooper et al, Peroxidase activity of hemoglobin towards ascorbate and urate: A synergistic protective strategy against toxicity of Hemoglobin-Based Oxygen Carriers (HBOC), Biochemica et Biophysica Acta 1784 (2008) 1415-1420.
Silaghi-Dumitrescu et al, "Ferryl haem protonation gates peroxidatic reactivity in globins", Biochem. J. (2007) 403, 391-395.
Reeder et al, "Tyrosine Residues as Redox Cofactors in Human Hemoglobin", The Journal of Biological Chemistry (2008), vol. 283, No. 45, pp. 30780-30787.
Stasio et al, "The importance of the effect of shear stress on endothelial cells in determining the performance of hemoglobin based oxygen carriers", Biomaterials XXX (2008) 1-7.
Cooper, "Radical Producing and Consuming Reactions of Hemoglobin: How Can We Limit Toxicity?", Artificial Organs (2009), 33(2):110-114.
International Search Report for PCT/GB2008/002199, mailed Nov. 5, 2008.
Reeder B J et al., "Tyrosine Residues as Redox Cofactors in Human Hemoglobin: Implications for Engineering Non Toxic Blood Substitutes", JBC Papers in Press, Aug. 26, 2008, pp. 1-17.
Reeder Brandon J et al., "Modulating Electron Transfer Pathways in Hemoglobin", Free Radical Biology & Medicine, & 14th Annual Meeting of the Society-For-Free-Radical-Biology-And-Medicine; Washington, DC, USA, Nov. 14-18, 2007, vol. 43, No. Suppl. 1, p. S27.

(Continued)

*Primary Examiner* — David Lukton
(74) *Attorney, Agent, or Firm* — Nixon & Vanderhye P.C.

(57) ABSTRACT

The present invention relates to a modified porphyrin-based oxygen-carrying protein, such as haemoglobin, which has been found, in its unmodified state to have a low affinity site of electron transfer and a high affinity electron transfer between a reductant and ferryl haem iron via one or more protein amino acids. The invention provides such proteins that comprise a modification to enhance this pathway.

10 Claims, 4 Drawing Sheets

(56) References Cited

OTHER PUBLICATIONS

Baudin-Creuza Veronique et al., "Additive Effects of Beta Chain Mutations in low Oxygen Affinity Hemoglobin BetaF41Y, K66T", Journal of Biological Chemistry, vol. 274, No. 36, Sep. 3, 1999, pp. 25550-25554.

Vasseur-Godbillon Corinne et al., "Recombinant Hemoglobin BetaG83C-F41Y.", The Febs Journal, Jan. 1, 2006, vol. 273, No. 1, pp. 230-241.

Griffon N et al., "Tetramer-Dimer Equilibrium of Oxyhemoglobin Mutants Determined from Auto-Oxidation Rates.", Protein Science: A Publication of the Protein Society Mar. 1998, vol. 7, No. 3, pp. 673-680.

Dumoulin A et al., "Two Mutations in Recombinant Hb Beta F41(C7)Y, K82 (EF6) Show Additive Effects in Decreasing Oxygen Affinity", Protein Science, Cambidge University Press, Cambridge, GB, vol. 1, No. 5, Jan. 1, 1996, pp. 114-120.

Baudin V et al., "Allosteric Properties of Haemoglobin Beta41 (C7) Phea Tyr: a Stable, Low-Oxygen-Affinity Variant Synthesized in *Escherichia coli*", Biochimica ET Biophysica Acta—Protein Structure and Molecular Enzymologie, Elsevier Science BV, Amsterdam, NL, vol. 1159, No. 2, Sep. 23, 1992, pp. 223-226.

Written Opinion of the International Searching Authority for PCT/GB2008/002199, mailed Nov. 5, 2008.

* cited by examiner

SEQUENCE LISTING

<160> NUMBER OF SEQ ID NOS: 8

<210> SEQ ID NO 1
<211> LENGTH: 141
<212> TYPE: PRT
<213> ORGANISM: Homo sapiens

<400> SEQUENCE: 1

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 2
<211> LENGTH: 146
<212> TYPE: PRT
<213> ORGANISM: Homo sapiens

<400> SEQUENCE: 2

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3
<211> LENGTH: 41

```
<212> TYPE: DNA
<213> ORGANISM: Artificial sequence
<220> FEATURE:
<223> OTHER INFORMATION: Synthetic sequence: Primer aY42V for

<400> SEQUENCE: 3
ccttcccaac caccaaaacc gtgttcccac actttgatct g            41

<210> SEQ ID NO 4
<211> LENGTH: 41
<212> TYPE: DNA
<213> ORGANISM: Artificial sequence
<220> FEATURE:
<223> OTHER INFORMATION: Synthetic sequence: Primer aY42V rev

<400> SEQUENCE: 4
cagatcaaag tgtgggaaca cggttttggt ggttgggaag g            41

<210> SEQ ID NO 5
<211> LENGTH: 41
<212> TYPE: DNA
<213> ORGANISM: Artificial sequence
<220> FEATURE:
<223> OTHER INFORMATION: Synthetic sequence: Primer aY42random for
<220> FEATURE:
<221> NAME/KEY: misc_feature
<222> LOCATION: (21)..(22)
<223> OTHER INFORMATION: n is a or g or c or t

<400> SEQUENCE: 5
ccttcccaac caccaaaacc nnkttcccac actttgatct g            41

<210> SEQ ID NO 6
<211> LENGTH: 41
<212> TYPE: DNA
<213> ORGANISM: Artificial sequence
<220> FEATURE:
<223> OTHER INFORMATION: Synthetic sequence: Primer aY42random rev
<220> FEATURE:
<221> NAME/KEY: misc_feature
<222> LOCATION: (20)..(21)
<223> OTHER INFORMATION: n is a or g or c or t

<400> SEQUENCE: 6
cagatcaaag tgtgggaamn nggttttggt ggttgggaag g            41

<210> SEQ ID NO 7
<211> LENGTH: 34
<212> TYPE: DNA
<213> ORGANISM: Artificial sequence
<220> FEATURE:
<223> OTHER INFORMATION: Synthetic sequence: Primer bF41Y for

<400> SEQUENCE: 7
ccgtggaccc agcgttactt tgaatccttc ggtg                    34

<210> SEQ ID NO 8
<211> LENGTH: 34
<212> TYPE: DNA
<213> ORGANISM: Artificial sequence
<220> FEATURE:
<223> OTHER INFORMATION: Synthetic sequence: Primer bF41Y rev

<400> SEQUENCE: 8
caccgaagga ttcaaagtaa cgctgggtcc acgg                    34
```

MODIFIED GLOBIN PROTEINS WITH ALTERED ELECTRON TRANSPORT PATHWAY

This application is the U.S. national phase of International Application No. PCT/GB2008/002199, filed 26 Jun. 2008, which designated the U.S. and claims priority to Great Britain Application No. 0712685.7, filed 29 Jun. 2007, the entire contents of each of which are hereby incorporated by reference.

FIELD OF THE INVENTION

The present invention relates to modified oxygen-carrying compounds such as haemoglobin and their use.

BACKGROUND TO THE INVENTION

Transfusion of a patient with donated blood has a number of disadvantages. Firstly, there may be a shortage of a patient's blood type. Secondly, there is a danger that the donated blood may be contaminated with infectious agents such as hepatitis viruses and HIV. Thirdly, donated blood has a limited shelf life. In addition, there are some situations where blood may not be readily available, such as in a battlefield or civil emergencies.

An alternative to transfusion involves the use of a blood substitute. A blood substitute is an oxygen carrying solution that also provides the oncotic pressure necessary to maintain blood volume. Two types of substitutes have recently been studied, fluorocarbon emulsions and haemoglobin solutions.

Haemoglobin as it exists within the red blood cell is composed of two alpha globin chains and two beta globin chains, each carrying a haem molecule. One alpha-like globin chain and one beta-like globin chain combine to form a dimer which is very stable. Alpha-like and beta-like globin genes belong to a family of related globin genes which are expressed at different stages of development and regulated by oxygen tension, pH, and the development from embryo to fetus to newborn. Two dimers then line up in antiparallel fashion to form tetramers. The binding of dimers to form the tetramers is not as strong as in the case of monomers binding to associate into dimers. The tetramers, therefore, have a tendency to fall apart to form dimers and there is always an equilibrium between tetramers, dimers, and monomers. At high concentrations of globin, the predominant form is the tetramer; with dilution, the dimer becomes the predominant form. This equilibrium is also affected by solvent, salts, pH and other factors as the binding forces are partly electrostatic.

There are obstacles however to using native haemoglobin as a blood substitute. Firstly, large dosages are required, requiring large scale production of protein, either by recombinant means or from donated human or recovered non-human blood. Secondly, it is important to obtain haemoglobin that is free from infectious agents and toxic substances. Thirdly, although haemoglobin is normally a tetramer of 68,000 molecular weight, it can dissociate to form alpha-beta dimers. The dimers are rapidly cleared by the kidneys and the residence time is much too short for cell-free haemoglobin to be useful as a blood substitute.

Several approaches have been taken to circumvent these difficulties. These include the expression of haemoglobin via recombinant DNA systems, chemical modification of haemoglobin, and the production of haemoglobin variants. Haemoglobin and variants of it have been expressed in various cellular systems, including *E. coli*, yeast and mammalian cells such as CHO cells.

A number of naturally-occurring variants of haemoglobin are known. Variants include: variants which autopolymerize, variants which prevent the dissociation of the tetramer, and variants that are stable in alkali. There are also over 30 naturally occurring haemoglobin variants which exhibit lowered oxygen affinity. Several examples of such variants are disclosed in WO 88/091799.

Another approach to improving the use of haemoglobin is the modification of this protein by the addition of further polymers to improve the stability of the protein in the blood. For example, U.S. Pat. No. 5,900,402 describes the use of non antigenic polymers, preferably polyalkylene oxide or polyethylene glycol.

Because haemoglobins (and indeed myoglobins or other oxygen-carrying proteins) are involved in oxygen transport and storage they are, as a consequence of this function (because of the redox properties of the iron ion present in the porphyrin ring of protein), responsible for the generation of reactive oxygen species. Autoxidation of the oxy derivative (Fe(II)) leads to non-functional ferric haem (Fe(III)) and superoxide ion ($O_2^{\cdot-}$), which subsequently dismutates to generate $H_2O_2$. These species can ultimately damage the protein and/or the haem group. An essential intermediate in the pathway leading to this damage is the ferryl haem (Fe(IV)=$O^{2-}$), itself formed through the reaction of the haem with $H_2O_2$ and lipid peroxides. A protein/porphyrin-based radical cation (P+•) accompanies the formation of the ferryl haem from ferric haem and peroxide as set out in equation (1):

$$P\text{—}Fe(III)+H_2O_2 \rightarrow P^{\cdot+}Fe(IV)=O^{2-}+H_2O \qquad (1)$$

Ferryl haem and the radical can also be extremely toxic, notwithstanding their transient existence. These oxidative cascades can be damaging because: (i) peroxide is a powerful oxidant known to produce cellular damage, (ii) both the ferryl haem and protein-based radicals can initiate oxidation of lipids, nucleic and amino acids by abstraction of hydrogen atoms, and (iii) haem modification can lead to highly toxic haem to protein-cross-linked species and to the loss of haem and the release of the 'free' iron.

The potential for haemoglobin-mediated peroxidative damage exists especially whenever the protein is removed from the protective environment of the erythrocyte. This would occur, for example, during spontaneous erythrocyte haemolysis or in haemolytic anaemias (e.g. sickle-cell anaemia). It has been shown that myoglobin induces kidney damage following crush injury (rhabdomyolysis) by exactly this peroxidative mechanism, rather than by free-iron catalysed Fenton chemistry as was thought previously (Holt et al, (1999) Increased lipid peroxidation in patients with rhabdomyolysis. *Lancet* 353, 1241; Moore, et al (1998) A causative role for redox) cycling of myoglobin and its inhibition by alkalinization in the pathogenesis and treatment of rhabdomyolysis-induced renal failure. *J. Biol. Chem.* 273, 31731-31737).

It has also been shown recently that haemoglobin can cause similar damage in vivo when it is released from the erythrocyte in subarachnoid haemorrhage (Reeder, et al (2002) Toxicity of myoglobin and haemoglobin: oxidative stress in patients with rhabdomyolysis and subarachnoid haemorrhage. *Biochem. Soc. Trans.* 30, 745-748). Furthermore, uncontrolled haem-mediated oxidative reactions of cell-free haemoglobin (developed as a blood substitute) have emerged as an important potential pathway of toxicity, either directly or via interactions with cell signalling pathways (Alayash, A. I. (2004) Oxygen therapeutics: can we tame haemoglobin? *Nat. Rev. Drug Discovery* 3, 152-159). The toxicity of ferryl haemoglobin has been demonstrated in an endothelial cell culture model system of ischaemia/reperfusion [McLeod, L. L. and Alayash, A. I. (1999) Detection of a ferryl-haemoglobin intermediate in an endothelial cell model after hypoxia-reoxygenation. *Am. J. Physiol.* 277, H92H99] and in cells that lack their antioxidant mechanisms such as glutathione (D'Agnillo & Alayash (2000) Interactions of haemoglobin with hydrogen peroxide alters thiol levels and course of endothelial cell death. *Am. J. Physiol. Heart Circ. Physiol.* 279, H1880-H1889).

Ferryl haemoglobin can cause cell injury, including apoptotic and necrotic cell death. Perfusion of rat intestine with chemically modified haemoglobin has been shown to cause localized oxidative stress, leading to leakage of the mesentery of radiolabelled albumin (Baldwin et al (2002) Comparison of effects of two haemoglobin-based $O_2$ carriers on intestinal integrity and co microvascular leakage. *Am. J. Physiol. Heart Circ. Physiol.* 283, H1292-H1301). Importantly, the cyanomet derivative of this haemoglobin, in which the haem iron is blocked with cyanide and is unavailable to enter a redox reaction, produced no cellular changes.

U.S. Pat. No. 5,606,025 describes the conjugation of haemoglobin to superoxide dismutase and/or catalase as one approach to reduce reperfusion injuries and other free-radical mediated processes associated with haemoglobin blood substitutes.

DISCLOSURE OF THE INVENTION

Our studies have investigated in further detail the mechanisms by which the ferryl (IV) species is generated in haemoglobin (Hb) and myoglobin (Mb), and the mechanisms by which this ion is responsible for the generation of oxidative stress.

We have discovered that myoglobin and haemoglobin from certain species (including human) show two distinct pathways of electron transfer from exogenous reductants to the ferryl haem iron. A low affinity pathway (typically >5 mM) represents direct electron transfer from the reductant to the ferryl haem iron in a hydrophobic pocket within the protein. A second high affinity pathway (typically <100 µM but often <10 µM) involves electron transfer between the reductant and ferryl haem iron via one or more protein amino acids. This high affinity through-protein pathway is present in native human myoglobin and haemoglobin alpha subunit, but absent in human haemoglobin beta subunits and *Aplysia* myoglobin. An example of an amino acid that allows this electron transfer is Tyr103 and Tyr42 in myoglobin and haemoglobin alpha chain respectively.

Our finding is based on observing commonalities in the profiles for the reduction of ferryl Mb by many iron chelators, which we have observed to have anti-oxidant properties. The effect of these reducing agents on the rate constant for ferryl decay plotted as a function of reductant concentration exhibits a complex curve that can be expressed as a double rectangular hyperbola function. We have also now found that more classical reducing agents such as ascorbate also show this double rectangular hyperbola concentration dependence. The two hyperbolae represent two binding sites for the reductant having differing affinities. Through the use of kinetic model, simulations and use of selected native and engineered proteins, we have interpreted this concentration dependence to represent two distinct electron transfer pathways from the reductant to the haem iron.

This high affinity pathway, though present in the alpha chain of haemoglobin, and in myoglobin, does not appear to be as active in other porphyrin-based oxygen-carrying proteins which lack a tyrosine residue at the equivalent to position 42. This is particularly the case with beta-haemoglobin.

According to the present invention, we propose the introduction of this pathway into such proteins by introduction of an amino acid equivalent to Tyr42, or any other residue able to constitute a high affinity electron transfer pathway to the ferryl ion. Such a modification will increase the ability of the ferryl ion to be reduced via this pathway. Effectively, such modifications expose the ferryl ion such that this ion may be more rapidly reduced and thus lessen its ability to damage surrounding tissues or substrates, such as lipids.

Thus the present invention provides a modified porphyrin-based oxygen-carrying protein, wherein said protein comprises a modification to enhance or introduce a high affinity electron transfer pathway to the ferryl ion.

The protein is preferably a haemoglobin beta chain (HO). The modification may be to Phe41, particularly wherein Phe41 is substituted by Tyr.

The invention also provides nucleic acids encoding these proteins, means for their production and the use of the proteins in methods of treatment. These and other aspects of the invention are described further herein below.

and beta (○) subunit calculated by fitting to a double exponential function. The alpha subunit, but not the beta subunit shows double rectangular hyperbola concentration dependence.

Figure 6:
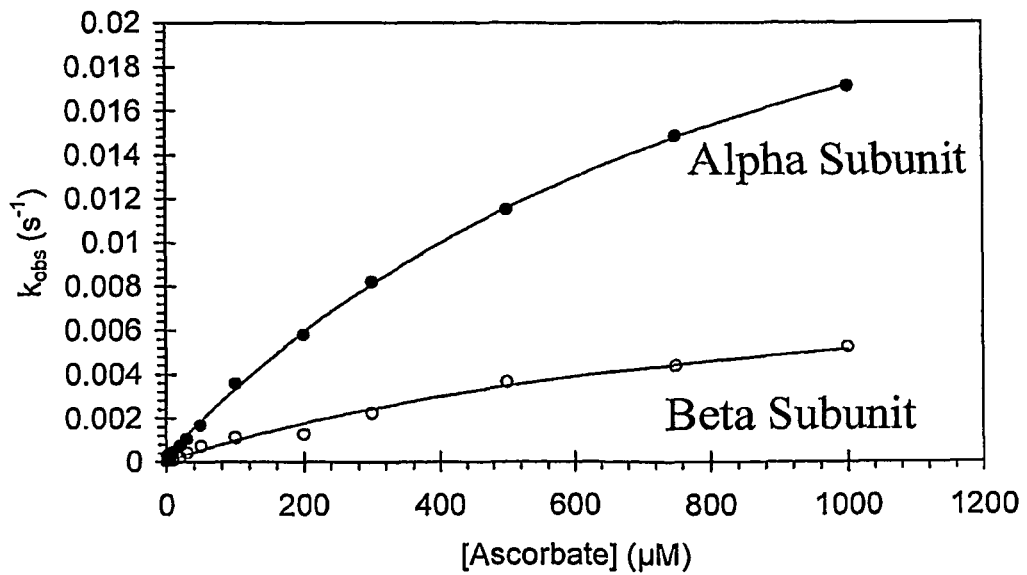

FIG. 6: Concentration dependence of recombinant α-Tyr42>Val ferryl human haemoglobin reduction by ascorbate. Ferryl myoglobin (10 μM) was reacted with ascorbate in sodium phosphate pH 7.4. Ferryl reduction rate constants for alpha subunit (●) and beta (○) subunit calculated by fitting to a double exponential function. Both the alpha subunit and beta subunit shows single rectangular hyperbola concentration dependencies.

Figure 7:
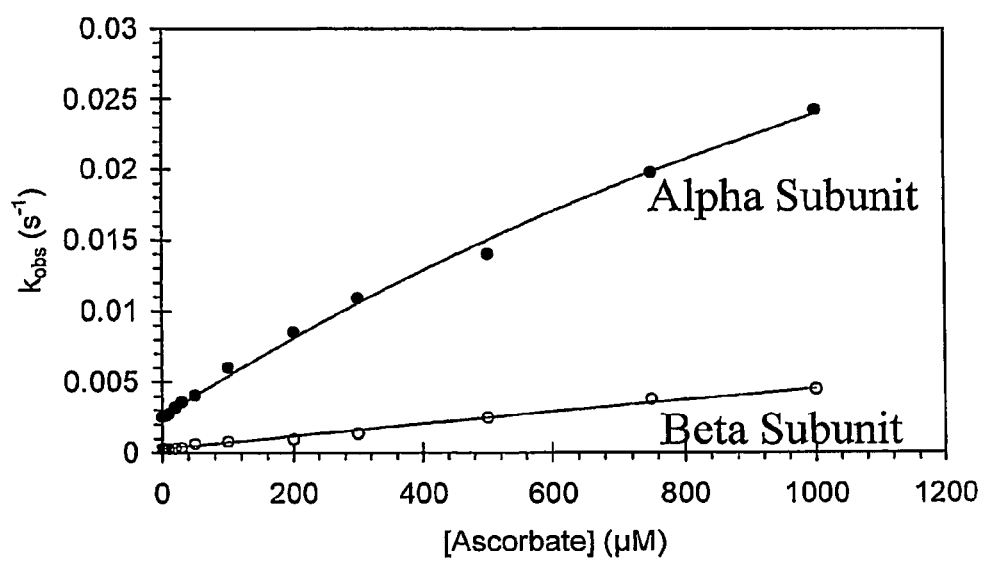

FIG. 7: Concentration dependence of recombinant α-Tyr42>Trp ferryl human haemoglobin reduction by ascorbate. Ferryl myoglobin (10 μM) was reacted with ascorbate in sodium phosphate pH 7.4. Ferryl reduction rate constants for alpha subunit (●) and beta (○) subunit calculated by fitting to a double exponential function. Both the alpha subunit and beta subunit shows single rectangular hyperbola concentration dependencies.

DETAILED DESCRIPTION OF THE INVENTION

Porphyrin-Based Oxygen-Carrying Protein

A porphyrin-based oxygen carrying protein refers to any polypeptide chain which in its native form carries a porphyrin molecule and which polypeptide, either alone or in a complex, carries and releases oxygen bound to the porphyrin molecule. Variants of such proteins, e.g. naturally occurring or synthetic mutants of wild-type porphyrin-based oxygen-carrying proteins are also contemplated by the invention.

The porphyrin-based oxygen-carrying protein will, in its native state, lack the high affinity oxygen transfer pathway present in the haemoglobin alpha subunit, e.g. the protein of SEQ ID NO:1 or its mammalian homologues. This pathway is mediated via an electron transfer pathway which includes a tyrosine residue at position 7 of the C helix. (As is known in the art, haemoglobin subunit proteins are also numbered by reference to the residues of individual helices or inter-helix resides, as set out in Table 1 below (based on U.S. Pat. No. 5,028,588 the contents of which are incorporated herein by reference). Tyr42 of human haemoglobin alpha chain is thus also identified in the art as residue C7. Accordingly, the equivalent residue in other haemoglobin alpha chains will also be in the C7 position.) The pathway is an electron transfer) between the reductant and ferryl haem iron via one or more protein amino acids. This high affinity through-protein pathway is present in native human myoglobin and haemoglobin alpha subunit, but absent in human haemoglobin beta subunits.

The oxygen-carrying proteins to be modified include mammalian haemoglobin subunits but may include non-mammalian haemoproteins and other genetically engineered proteins where the protein is altered to carry oxygen. These proteins will be recombinant, having altered sequences (substitution of amino acid residues, but may also include insertion of residues) to introduce a high affinity through-protein electron pathway from reductants in the bulk solution to the haem ferryl iron.

It is expected that by introducing the high affinity pathway in proteins such as human haemoglobin beta subunit we will be able to decrease the toxicity of blood substitutes by allowing reductants that are administered with the blood substitute such as ascorbate, urate or deferiprone to more rapidly reduce the highly toxic ferryl oxidation state of these haemoproteins and thus limiting oxidation of substrates such as lipids and DNA.

Thus the invention is applicable to any haemoglobin subunit which in its natural state does not have the high-affinity pathway. In one aspect, the protein is human haemoglobin beta chain, whose sequence is set out as SEQ ID NO:2 below. Other haemoglobin subunits which may be used are those which are vertebrate or non-vertebrate haemoglobin subunits that do not have a tyrosine residue at a position equivalent to residue 42/C7.

Vertebrate haemoglobins include mammalian haemoglobins. Mammalian haemoglobins are particularly highly conserved. Examples of homologues to the human beta chain include members of the beta globin superfamily, such as gamma or delta haemoglobin found in haemoglobin F (HbF) or haemoglobin A2 (HbA2) respectively. These and other non-limiting examples of such homologues include the mammalian species homologues of Table 2, all of which also have a Phe42 residue. The sequences may be obtained from on-line databases including via the Research Collaboratory for Structural Bioinformatics protein databank (pdb). These pdb references provide sequences for the haemoglobin beta-family subunit proteins and, where applicable, a corresponding alpha subunit protein. The beta-family subunit sequence may be used either with its corresponding alpha subunit or alone, or in combination with another beta-family subunit protein.

TABLE 2

| Species | PDB Code |
|---|---|
| Human (*Homo sapiens*) HbF | 1FDH |
| Human (*Homo sapiens*) HbA2 | 1SI4 |
| Bovine (*Bos taurus*) | 1G09 |
| Pig (*Sus scrofa*) | 2PGH |
| Horse (*Equus caballus*) | 1NS6 |
| Maned Wolf (*Chrysocyon brachyurus*) | 1FHJ |
| Deer (*Odocoileus virginianus virginianus*) | 1HDS |
| Donkey (*Equus asinus*) | 1S0H |
| Crab Eating Fox (*Cerdocyon thous*) | 2B7H |

Other vertebrate haemoglobins alpha subunit homologues include avian, reptile and fish haemoglobins having a residue equivalent to Phe42. Non-limiting examples of such subunits include those given in Table 3, which indicates in column 3 the position of the amino acid residue homologous to Phe42 of mammalian beta chain subunits.

TABLE 3

| Species | PDB Code | Phe 42 Equivalent Residue |
|---|---|---|
| Avian: | | |
| Bar Headed Goose (*Anser indicus*) | 1A4F | Phe41 |
| Graylag Goose (*Anser anser*) | 1FAW | Phe41 |
| Chicken (*Gallus gallus*) | 1HBR | Phe41 |
| Reptile: | | |
| Giant Tortoise (*Geochelone gigantean*) | 1V75 | Phe41 |
| Fish: | | |
| Akaei (*Dasyatis akajei*) | 1CG5 | Phe42 |
| Antarctic fish (*Pagothenia bernacchii*) | 1PBX | Phe42 |

Other non-vertebrate eukaryote beta haemoglobin homologues may be identified in arthropods or other multicellular organisms (e.g. molluscs, nematode worms and non-nematode worms) and those of unicellular organisms.

Modification of the Oxygen-Carrying Protein

The oxygen carrying protein may be modified by substitution or insertion to introduce a high-affinity electron transfer pathway.

Figure 5:
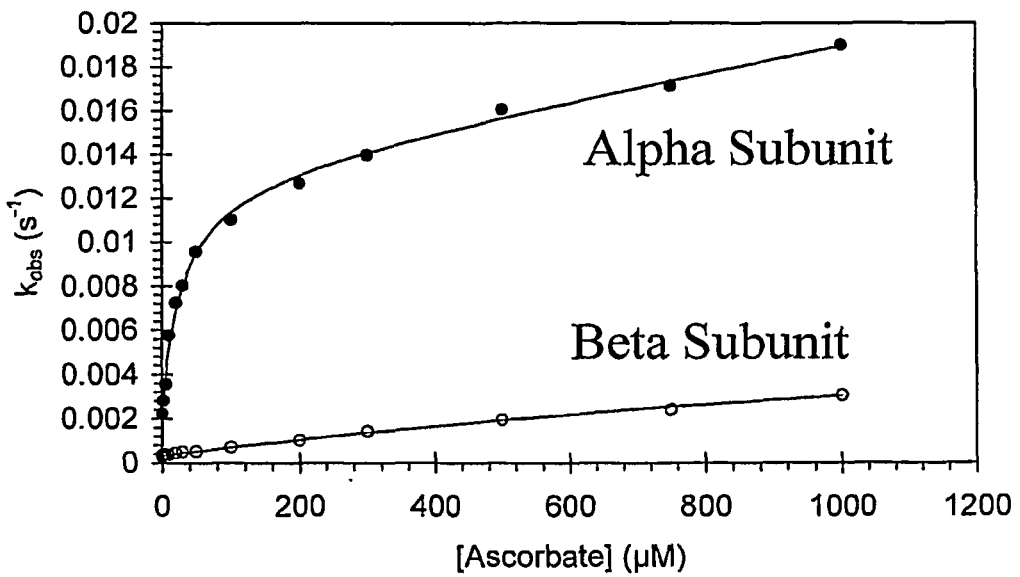
FIG. 5: Concentration dependence of wild type ferryl human haemoglobin reduction by ascorbate. Ferryl myoglobin (10 µM) was reacted with ascorbate in sodium phosphate pH 7.4. Ferryl reduction rate constants for alpha subunit (●)

In particular and as illustrated in FIG. 5, the phenylalanine of the beta subunit of haemoglobin is located close to the haem and is surface exposed making it ideal to act as an electron conduit from exogenous reductants to the ferryl haem iron were it to be a redox-active group. Thus the invention provides an insertion or substitution to provide a redox-active residue at a similar position.

The redox-active amino acid may be, for example, tyrosine, tryptophan or histidine. Tyrosine is particularly preferred.

Thus in one aspect the invention provides a mammalian beta globin subunit modified to position a redox-active residue in the protein such that protein exhibits a high affinity electron transfer pathway. The presence of this pathway may be observed by showing that the protein has a double rectangular hyperbola concentration dependence to reducing agents.

In one aspect, the C7 position is substituted to introduce a redox-active amino acid, particularly those mentioned above. The beta globin subunit alternatively may include an insertion to introduce this residue into the protein, e.g. into the C helix, e.g. between the C6 and C7 residues, or between the C7 and CD1 residues. Such an insertion may be combined with a further modification of the C helix of the protein, e.g. a deletion or substitution of a residue in the C1 to C6 positions.

Molecular modelling methods may be used to identify other positions in the beta chain of mammalian haemoglobins which are also located near the ferryl haem iron and which may be substituted to introduce a redox-active amino acid.

Other Modifications

In one embodiment, in addition to the attenuating modification of a wild-type oxygen-carrying protein, the protein may comprise one or more (for example from one to five, such as one or two) additional substitutions, or a deletion or insertion of from one to five, such as one, two or three amino acids (which may be contiguous or non-contiguous). These may be variations which affect a further property of the protein, such as its oxygen affinity or cooperativity, enhancements in stability and assembly rates, decreased heme loss rates or autoxidation rates, or resistance to proteolytic degradation and aggregation, its binding to nitric oxide or its ability to be produced in a soluble form by recombinant means. Such modifications are known in the art per se and may be incorporated into the proteins of the present invention.

In a preferred aspect, the modification is one which reduces the binding of nitric oxide (NO). A number of haemoglobin variants which limit NO binding while still permitting oxygen transport are known. A number of variants of haemoglobin beta chains which have reduced rates of reaction with nitric oxide are disclosed in U.S. Pat. No. 6,455,676, the contents of which are incorporated herein by reference.

In particular, the following changes may be included in the oxygen carrying protein in addition to the attenuating modification:

B13(Leu>Phe or Trp); G12(Leu>Phe or Trp); B10(Leu>Phe) and E4(Val>Leu); B10(Leu>Trp) and E4(Val>Leu); B14(Leu>Phe or Trp); G8(Leu>Phe) and G12(Leu>Trp); E11(Val>Leu) and G8(Leu>Trp); E11(Val>Trp) and G8(Leu>Met); E11(Val>Leu) and G8(Leu>Phe); E11(Val>Leu) and G8(Leu>Met); E11(Val>Phe) and G8(Leu>Ile); E11(Val>Phe) and G8(Leu>Phe); E11(Val>Phe) and G8(Leu>Trp); E11(Val>Phe) and G8(Leu>Met); E11(Val>Met) and G8(Leu>Trp); E11(Val>Met) and G8(Leu>Trp) and E7(His>Gln); E11(Val>Trp) and G8(Leu>Ile); E7(His>Gln) and E11(Val>Trp); E7(His>Gln) and E11(Val>Leu); E7(His>Gln) and E11(Val>Phe); E7(His>Gln) and E11(Val>Phe) and G8(Leu>Phe or Trp); E7(His>Gln) and E11(Val>Leu or Trp) and G8(Leu>Phe or Trp); E11(Val>Trp or Phe) and G12(Leu>Trp or Met); E11(Val>Trp or Phe) and B13(Leu>Trp or Met); B10(Leu>Trp) and B13(Leu>Trp or Met); B10(Leu>Phe) and B13(Leu>Trp); B10(Leu>Trp or Phe) and G12(Leu>Trp); B10(Leu>Phe) and G12(Leu>Met); G8(Leu>Trp) and G12(Leu>Trp or Met); or G8(Leu>Trp) and B13(Leu>Trp or Met).

The numbering used above is based on helix chain numbering, which can be cross-referenced to the primary sequence numbering of Table 1 for the human beta chain. These modifications at equivalent positions in other oxygen carrying proteins may also be made.

Protein Multimers

In one embodiment, oxygen-carrying proteins are present in multimeric forms. Such forms may prolong life of the protein in circulation, improve oxygen-carrying capacity or reduce side-effects.

In the case of haemoglobin beta subunit proteins such forms include a tetrameric haemoglobin protein. In this form two beta chains may form a tetramer with two alpha chains. Optionally, two or more of the subunits may be covalently linked to each other, e.g. via chemical cross-linking or as a result of recombinant expression.

The alpha chains may be wild type alpha chains, e.g. a human alpha chain of SEQ ID NO:1 or a homologous vertebrate or non-vertebrate alpha chain. Vertebrate alpha chains include mammalian, avian, reptile and fish alpha chains. Such alpha chains include those found with their associated with the beta chains referred to above in Tables 2 to 4 and whose sequences are obtainable from the pdb entries.

The alpha chains may comprise one or more (for example from one to five, such as one or two) additional substitutions, or a deletion or insertion of from one to five, such as one, two or three amino acids (which may be contiguous or non-contiguous). These may be variations which affect a further property of the protein, such as its interaction with other proteins, its binding to nitric oxide or to facilitate its production by recombinant means.

In one aspect, the alpha chain may be modified to remove tyrosine residue at position 42, e.g. by deletion or by substitution with a redox-inactive residue. Amino acids which are contemplated here as redox-inactive residues include alanine, arginine, asparagine, aspartic acid, cysteine, glutamic acid, glutamine, glycine, isoleucine, leucine, lysine, methionine, phenylalanine, proline, serine, threonine and valine Particular changes to the alpha-chain contemplated which modify binding to nitric oxide include E11(Val>Leu) and E7(His>Gln); E11(Val>Phe or Trp) and E7(His>Gln); E11(Val>Phe or Trp or Leu) and E7(His>Gln) and G8(Leu>Phe or Trp); B10(Leu>Phe) and E4(Val>Leu); B10(Leu>Trp) and E4(Val>Leu); B10(Leu>Trp) and E7(His>Gln); B10(Leu>Trp) and E11(Val>Phe); B10(Leu>Trp) and E11(Val>Trp); B10(Leu>Trp) and E11(Val>Leu) and G8(Leu>Trp); B10(Leu>Trp) and E11(Val>Leu) and G8(Leu>Phe); B10(Leu>Trp) and E11(Val>Phe) and G8(Leu>Trp); B10(Leu>Trp) and E11(Val>Phe) and G8(Leu>Ile); B10(Leu>Trp) and E7(His>Gln) and E11(Val>Leu) and G8(Leu>Trp); B10(Leu>Trp) and E11(Val>Trp) and G8(Leu>Trp); E11(Val>Leu) and G8(Leu>Phe); E11(Val>Leu) and G8(Leu>Trp); B13(Met>Phe or Trp); G12(Leu>Phe or Trp); or B14(Phe>Trp)).

The numbering used above is based on helix chain numbering, which can be cross-referenced to the primary sequence numbering of Table 1 for the human alpha chain. These modifications at equivalent positions in other oxygen carrying proteins may also be made.

Other higher order forms, either covalently or non-covalently associated with each other and/or with other oxygen-carrying proteins may also be provided. For example, polymerized haemoglobin subunit chains or cross-linked chains are known in the art per se and these approaches may be applied to the present invention.

Protecting Groups

In another aspect, the oxygen-carrying proteins of the invention, whether in monomeric or multimeric form, may be conjugated to a protecting group. Various types of protecting groups are known as such in the art and may be used in the present invention. Where the protecting group is a protein, this protecting group may be produced as a fusion, e.g. at the N- or C-terminus of the oxygen-carrying protein. Alternatively, the protein may be co-expressed with the oxygen-carrying protein or expressed separately, and the two proteins joined by chemical) means using a cross-linker.

For example, one class of protecting groups are enzymatic anti-oxidant proteins. These include catalase and superoxide dismutase (SOD). Any suitable catalase or SOD may be used, though preferably these are human enzymes. The enzymes may be produced recombinantly or by any other means conventional in the art.

U.S. Pat. No. 5,606,025, the contents of which are incorporated herein by reference, describes the conjugation of such enzymes to a haemoglobin and such methods may be used in the present invention. Thus any suitable inert cross-linking reagent previously reported as suitable for preparing cross-linked haemoglobin for use as an oxygen-carrying resuscitative fluid can be used, for example glutaraldehyde, diasprin derivatives, polyaldehydes including those derived from oxidative ring-opening of oligosaccharides, diphosphate esters, triphosphate esters, etc. The enzymes of interest have chemical groups similar to those on the globin chains of haemoglobin so that they will appropriately chemically bind to the haemoglobin as it cross-links by reaction with the cross-linking reagent.

Relative amounts of the oxygen-carrying protein and the enzymatic anti-oxidant protein can vary over wide limits, with the oxygen-carrying protein constituting the major component. The total weight of the enzyme(s) is suitably in the approximate range of 0.1-10% based on the weight of the oxygen-carrying protein, and preferably in the approximate range 0.5-2.5%. When, as in one embodiment, both SOD and catalase are chemically bound to the polyhaemoglobin, the weight ratio of SOD to catalase is suitably from about 1:1 to 5:1 and preferably from about 1.5:1 to 2.5:1.

Another class of protecting group, which may be used as well as the above-described enzymatic groups, or in the alternative, is a non-antigenic polymeric group such as a polyalkylene oxide protecting group. Such groups may also be used on monomeric oxygen-carrying proteins or these proteins when in dimeric or higher form.

For example, U.S. Pat. No. 5,900,402, the contents of which are incorporated herein by reference, describes the conjugation of polyalkylene oxides, most preferably polyethylene glycol (PEG) to oxygen-carrying proteins.

The conjugate is preferably formed by covalently bonding a hydroxyl terminal of the polyalkylene oxide and the free amino groups of lysine residues of the oxygen-carrying protein. See, for example, U.S. Pat. No. 5,234,903, which discloses mPEG-succinimidyl carbonate-Hb conjugates. Other methods for conjugating the polymers with oxygen-carrying proteins are known in the art as such, such as by via an amide or ester linkage, are also suitable for use with the present invention. While epsilon amino group modifications of haemoglobin lysines are preferred, other conjugation methods are also contemplated. Covalent linkage by any atom between the haemoglobin and polymer is possible. Moreover, non-covalent conjugation such as lipophilic or hydrophilic interactions are also contemplated.

Additional examples of activated polymers which are suitable for covalently conjugating the oxygen carrying proteins are described in U.S. Pat. Nos. 5,349,001; 5,321,095; 5,324,844 and 5,605,976 as well as PCT Publication Numbers WO95/11924 and WO96/00080, the disclosure of each of which is incorporated herein by reference.

The conjugates preferably include polyethylene glycol (PEG) as the polyalkylene oxide. The polyalkylene oxides include monomethoxy-polyethylene glycol, polypropylene glycol, block copolymers of polyethylene glycol and polypropylene glycol and the like. The polymers can also be distally capped with $C_{2-4}$ alkyls instead of monomethoxy groups.

To be suitable for use herein, the polyalkylene oxides must be soluble in water at room temperature. Polyalkylene oxide strands having a (number average) molecular weight of from about 200 to about 100,000 Daltons can be used. For example, preferable PAOs have molecular weights of from about 1,000 to about 30,000 while PAOs having a molecular weight of from about 2,000 to about 25,000 are more preferred. Some particularly preferred conjugates of the present invention include polyalkylene oxide strands having a molecular weight of about 5,000 Daltons.

The ratio of the number of strands of the non-antigenic polymeric group to the oxygen-carrying protein may be from about 1:1 to about 20:1, preferably from about 5:1 to 15:1, for example about 10:1. The strands may be of the size ranges specified above.

Overall, the molecular weight of a monomer of an oxygen-carrying protein prior to conjugation is about 17,000 Da. Where such a protein is conjugated to a non-antigenic polymeric group as described above, the conjugate will be from about 30% to 60%, such as about 45% to 55% by weight of protein (i.e. the oxygen-carrying protein or a conjugate of this protein and an enzymatic group), the remainder being the non-antigenic polymeric group.

An exemplary embodiment of the invention is thus a conjugate of an oxygen-carrying protein of to the invention and 45% to 55% by weight of polyalkylene oxide having a molecular weight of from about 2,000 to about 25,000. In one aspect of this embodiment, the oxygen-carrying protein may be a haemoglobin beta chain in which the modification is at Phe41. In another aspect of this embodiment, the polyalkylene oxide is PEG. In a further aspect, the oxygen-carrying protein is a haemoglobin alpha chain in which the attenuating modification is at Phe41 and the polyalkylene oxide is PEG.

In the above embodiments, the oxygen-carrying protein may be in the form of a monomer or a polymer of two or more units.

Compositions

The oxygen-carrying proteins of the invention are desirably formulated as a composition comprising a physiologically acceptable carrier, suitable for administration to a mammal, particularly a human. Generally, such a carrier will be a sterile solution which comprises buffers and preservatives used to keep the solution at physiological pH and stable during storage. The carriers may be such physiologically compatible buffers as Hank's or Ringer's solution, physiological saline, a mixture consisting of saline and glucose, and heparinized sodium-citrate-citric acid-dextrose solution. The oxygen-carrying proteins of the present invention can be mixed with colloidal-like plasma substitutes and plasma expanders such as linear polysaccharides (e.g. dextran), hydroxyethyl starch, balanced fluid gelatin, and other plasma proteins. Additionally, the oxygen-carrying proteins may be mixed with water soluble, physiologically acceptable, polymeric plasma substitutes, examples of which include polyvinyl alcohol, poly(ethylene oxide), polyvinylpyrrolidone, and ethylene oxide-polypropylene glycol condensates.

Compositions of the invention may further include one or more compounds with anti-oxidant properties. These compounds may include ascorbate and urate. The anti-oxidant may be included at any suitable concentration, which may vary according to intended use and the nature of the anti-oxidant. For example, a suitable concentration of urate may be in the range of from 50 to 400 micromolar, and for ascorbate of from 50 to 200 micromolar, though lower or higher amounts may be used if need be.

The compositions may also include iron chelating agents which may play a role in sequestering iron released by the breakdown of the oxygen-carrying protein. Examples of such iron chelating agents include desferrioxamine and deferiprone. The iron chelating agent, or mixture thereof, may be present at a concentration of, for example, 10-5000 micromolar.

Administration of Oxygen-Carrying Proteins

Proteins of the invention may be used as blood substitutes. There are numerous conditions in which it will be useful for restoration, maintenance or replacement of oxygen levels is required. These include trauma; ischemia (such as ischemia induced by heart attack, stroke, or cerebrovascular trauma); haemodilution, where a blood substitute is required to replace blood that is removed pre-operatively; septic shock; cancer (e.g. to deliver oxygen to the hypoxic inner core of a tumour mass); chronic anaemia; sickle cell anaemia; cardioplegia; and hypoxia. Thus the oxygen-carrying proteins, and compositions thereof, of the present invention may be used in methods for the treatment of the above-mentioned conditions.

The oxygen-carrying proteins, and compositions thereof, of the present invention may also be used ex vivo in organ perfusion. Blood substitutes may be particularly useful in the organ perfusion, where maintaining oxygen content in an organ ex vivo prior to transplantation is required to sustain the organ in an acceptable condition. Organs include heart, liver, lung, kidneys.

The concentration and amount of oxygen-carrying protein of the invention used in any of the above-mentioned methods will be at the discretion of the physician, taking account of the nature of the condition of the patient and the treatment. Typically, the oxygen-carrying protein may be used at a concentration of from 0.1 to 6 g/dl, e.g. from 0.1 to 4 g/dl. The oxygen-carrying protein will usually be administered intravenously.

Co-administration of an innocuous reagent to enhance nitric oxide production (e.g. arginine) is also envisaged.

Nucleic Acids

The invention also provides nucleic acids encoding the modified oxygen-carrying proteins of the invention. The nucleic acid may be DNA or RNA. The DNA may be single- or double-stranded.

The nucleic acid of the invention may in isolated and/or purified form, or free or substantially free of material with which it is naturally associated, such as free or substantially free of nucleic acid flanking the gene in the human genome, except possibly one or more regulatory sequence(s) for expression.

Generally, nucleic acids of the invention may be obtained by modification of wild-type sequences encoding the oxygen-carrying protein. The nucleic acid sequences of wild-type haemoglobins and other oxygen carrying proteins are known in the art and widely available. Generally, recombinant techniques such as site-directed mutagenesis may be used to modify a known wild-type sequence such that the sequence encodes a modified oxygen-carrying protein of the invention.

The wild-type sequence of a mammalian nucleic acid may also be modified to optimize codon usage for expression in a heterologous system, e.g. in bacterial or yeast cells.

A nucleic acid of the invention may be incorporated into a recombinant replicable vector. The vector may be used to replicate the nucleic acid in a compatible host cell. Thus in a further embodiment, the invention provides a method of making a nucleic acid of the invention by introducing a nucleic acid of the invention into a replicable vector, introducing the vector into a compatible host cell, and growing the host cell under conditions which bring about replication of the vector.

Preferably, a nucleic acid of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage phagemid or baculoviral, cosmids, YACs, BACs, or PACs as appropriate. Vectors include gene therapy vectors, for example vectors based on adenovirus, adeno-associated virus, retrovirus (such as HIV or MLV) or alpha virus vectors.

The vectors may be provided with an origin of replication, optionally a promoter for the expression of the oxygen-carrying protein and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoter. Mammalian promoters include the metallothionein promoter which is can be induced in response to heavy metals such as cadmium. Viral promoters such as the SV40 large T antigen promoter or adenovirus promoters may also be used. All these promoters are readily available in the art.

The vectors may include other sequences such as promoters or enhancers to drive the expression of the inserted nucleic acid, nucleic acid sequences so that the oxygen-carrying protein is produced as a fusion and/or nucleic acid encoding secretion signals so that the polypeptide produced in the host cell is secreted from the cell.

Vectors for production of polypeptides of the invention for use in gene therapy include vectors which carry a mini-gene sequence of the invention.

Host Cells and Production of Oxygen-Carrying Proteins

Host cells according to the invention such as those mentioned herein above may be cultured under conditions to bring about expression of the oxygen-carrying protein, followed by recovery of the protein to provide the protein in substantially isolated form.

The protein may be produced with a source of haem or may be mixed with a suitable source of haem such as ferro-protoporphyrin or ferri-protoporphyrin (hemin) during or after recovery in order to provide a functional oxygen-carrying protein.

For example, U.S. Pat. No. 5,801,019, the contents of which are incorporated herein by reference, describes expression and recovery of various modified haemoglobins, including multimers of haemoglobin subunits, in yeast cells. Such methods may be used in the present invention for the production of the oxygen-carrying proteins.

Where the oxygen-carrying protein is a haemoglobin beta chain subunit, it may be co-expressed with complementary subunits, e.g. a alpha chain subunit. The co-expressed protein may be in the form of a separate protein or a fusion with the beta chain subunit.

Following expression, the proteins are recovered using standard methods including but not limited to chromatography (e.g., ion exchange, affinity, and sizing column chromatography), centrifugation, differential solubility, or by any other standard technique for the purification of proteins.

EXAMPLES

The present invention is illustrated further by the following examples.

Example 1

Myoglobin from Horse, but not *Aplysia*, possesses a high affinity through-protein electron transfer pathway as measured by ferryl reduction kinetics In this example the kinetics of the reduction of ferryl haem from myoglobin from different species to ferric haem protein were examined kinetically to determine the presence or absence of a high affinity-through protein pathway. Following the procedure, ferric horse myoglobin from Sigma-Aldrich (Poole, Dorset, UK, further purified by gel filtration), or recombinant ferric *Aplysia* myoglobin Mb (20 μM) in 5 mM sodium phosphate pH 7.4 was reacted with $H_2O_2$ (20 μM) at 25° C. for 15 min. At this time conversion of ferric myoglobin to ferryl myoglobin was greater than 95% as measured by addition of sodium sulfide (1 mM). Catalase (10 nM) was added to remove unreacted $H_2O_2$ and was left to react for a further 1 min. At the pH used the ferryl haem protein is stable for several hours. Reductant was then added in 0.1M sodium phosphate pH 7.4 in a 1:1 volume ratio so that final concentration of ferryl myoglobin was 10 μM. The pH may be 'jumped' to other values where the ferryl haem is unstable using other strong buffers (e.g. 0.1M sodium acetate, pH 5). The optical spectrum was followed until reaction was complete. The time course (425 nm-408 nm) was fitted to a single exponential function using the least squares method. These rate constants were then plotted as a function of reductant concentration and this profile fitted (least squares method) to a double rectangular hyperbola (FIG. 1):

$$k_{obs} = \frac{k_a[S]}{[S]+K_{D1}} + \frac{k_b[S]}{[S]+K_{D2}} + A_R$$

Where $k_a$ and $k_b$ are the maximum rates for each hyperbola and $K_{D1}$ and $K_{D2}$ are the dissociation constants, S is the concentration of the reductant and $A_R$ is the rate constant for ferryl auto-reduction.

The dependence of the concentration of reductant on the changes in the observed rate constant for ferryl myoglobin reduction from horse shows a double rectangular hyperbola dependence that is not observed in *Aplysia* myoglobin. Myoglobin from horse has two tyrosine residues at positions 103 and 146, while *Aplysia* myoglobin has no tyrosine residues.

Example 2

A tyrosine residue close to the haem is key to the high affinity through-protein electron transfer pathway.

Figure 2:
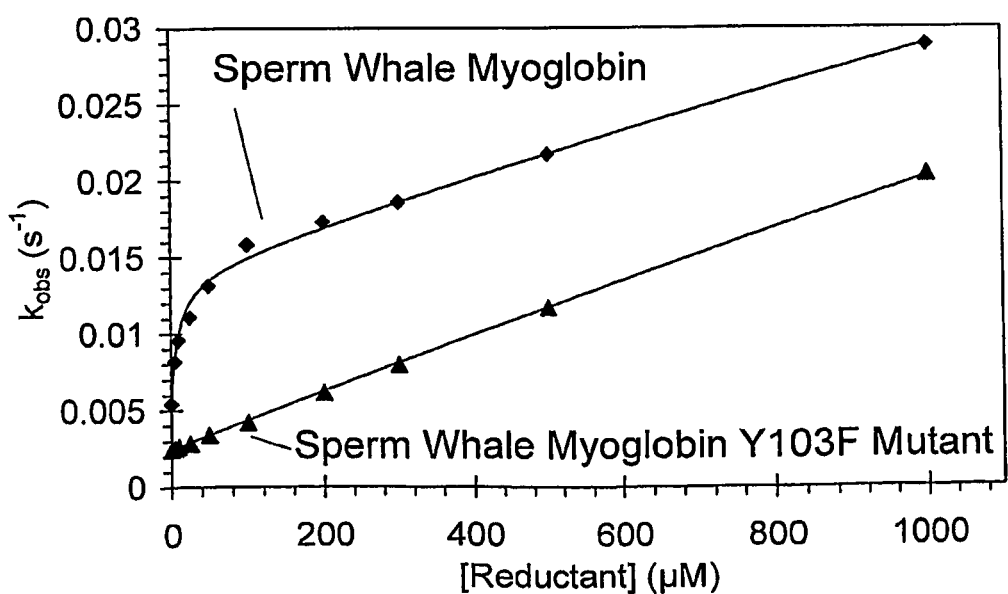
FIG. 2: Concentration dependence of recombinant sperm whale myoglobin with reducing agent deferiprone. Wild type sperm whale myoglobin (♦), but not the Tyr103>Phe mutant of sperm whale myoglobin (▲), shows a double rectangular hyperbola concentration dependence.

Wild-type and recombinant sperm whale myoglobin and recombinant Tyr103>Phe sperm whale myoglobin were reacted with peroxide and the kinetics of ferryl haem reduction by deferiprone determined as described in example 1. The through-protein electron transfer pathway, evident in wild type sperm whale myoglobin, is not observed in the Tyr103>Phe mutant (FIG. 2). This demonstrates that the presence of a redox active tyrosine, interfacing the haem and the external environment, is a key component for the high affinity pathway.

Figure 1:
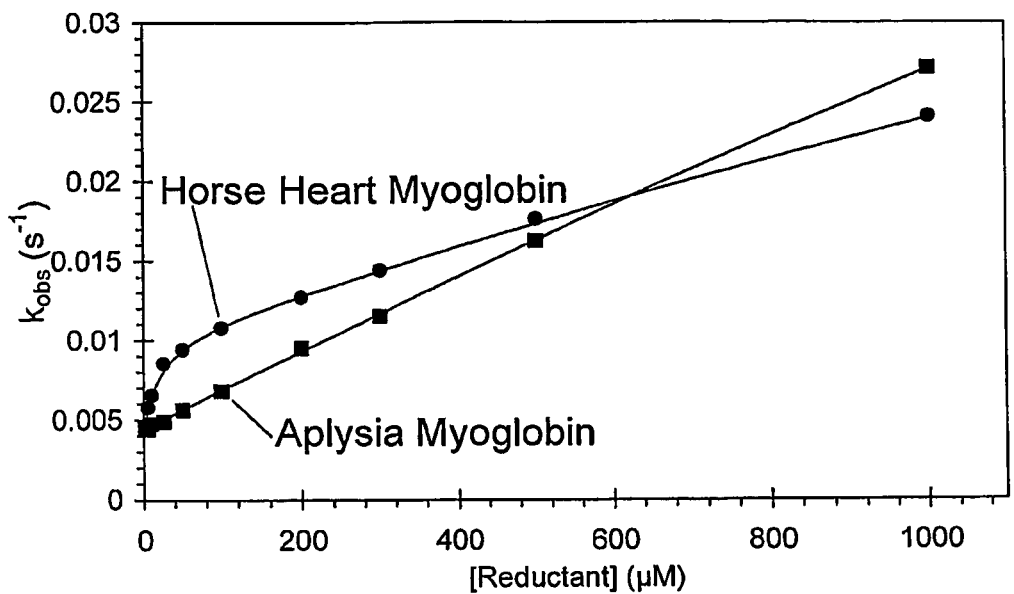
FIG. 1: Concentration dependence ferryl reduction of different myoglobin species with reducing agent deferiprone. Horse myoglobin (●), but not *Aplysia* myoglobin (■), shows a double rectangular hyperbola concentration dependence.
Figure 3:
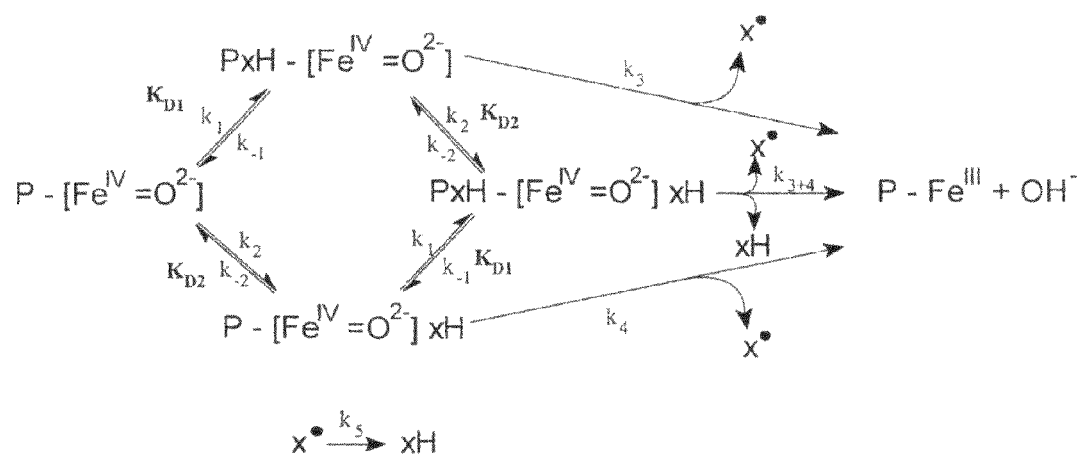
FIG. 3: The proposed two site model for reduction of a haemoprotein possessing a high affinity through protein electron transfer pathway. Reductant (xH) binds to two possible sites on myoglobin in its ferryl oxidation state (P—[Fe(IV)=$O^{2-}]^{2+}$, where P denotes protein) with affinities $K_{D1}$ and $K_{D2}$. Only from these two sites can electron transfer from the reductant to the ferryl iron take place. The high affinity binding site is situated at, or close to, tyrosine 103 (PxH—[Fe(IV)=$O^{2-}$]), allowing the transfer of an electron ($k_{max}$≈0.01 $s^{-1}$) through the protein to the ferryl haem iron to generate the ferric protein (P—Fe(III)). The low affinity site is situated in the haem pocket allowing electron transfer directly between the reductant and the ferryl haem (P—[Fe(IV)=$O^{2-}$]xH). This model also allows both sites being filled by reductant (PxH—[Fe(IV)=$O^{2-}$]xH). For the kinetic simulations it is assumed that the binding on one site will not affect the affinity of binding to the second site. The model also incorporates a step in which the oxidized reductant may be regenerated.
Figure 4:
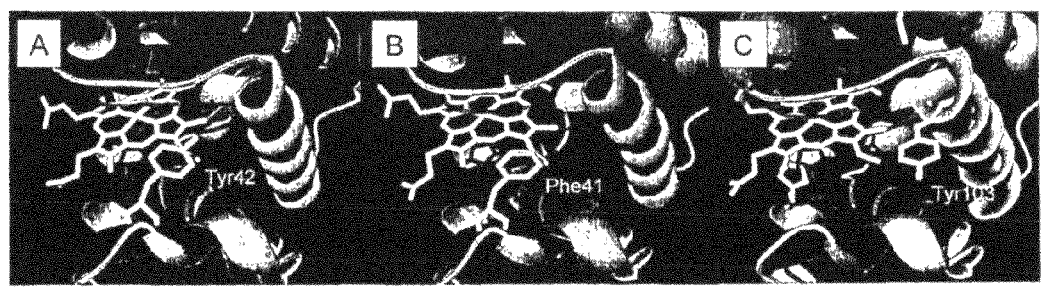
FIG. 4: Position of residues that can introduce or eliminate through-protein electron transfer in alpha human haemoglobin (A), beta human haemoglobin (B) with comparison of known electron conduit residue Tyr103 of horse myoglobin (C) from crystal structures. Tyr103 of horse myoglobin is close to the haem and is surface exposed making it ideal to act as an electron conduit from exogenous reductants to the ferryl haem iron. Human haemoglobin alpha subunit has a tyrosine in approximately the same spatial environment (Tyr42), however this residue in human haemoglobin beta is a redox-inactive phenylalanine.

The data from FIGS. 1 and 2 can be rationalised by a two site model where a reductant (xH) binds to two possible sites on myoglobin in its ferryl oxidation state (P—[Fe(IV)= $O^{2-}]^{2+}$, where P denotes protein, FIG. 3) with affinities $K_{D1}$ and $K_{D2}$. Only from these two sites can electron transfer from the reductant to the ferryl iron take place. The high affinity binding site is situated at, or close to, Tyr103 (PxH—[Fe(IV)=$O^{2-}$]), allowing the transfer of an electron ($k_{max}$≈0.01 $s^{-1}$) through the protein to the ferryl haem iron to generate the ferric protein (P—Fe(III)). The low affinity site is situated in the haem pocket allowing electron transfer directly between the reductant and the ferryl haem (P—[Fe(IV)=$O^{2-}$]xH). This model also allows both sites being filled by reductant (PxH—[Fe(IV)=$O^{2-}$]xH). For the kinetic simulations it is assumed that the binding on one site will not affect the affinity of binding to the second site. The model incorporates a step in which the oxidized reductant may be regenerated. This model also allows predictions on other haem proteins based on crystal structures. The structure of alpha subunit of human haemoglobin shows a tyrosine in a similar spatial position (Tyr42) compared to myoglobin, close to the haem and is surface exposed making it ideal to act as an electron conduit from exogenous reductants to the ferryl haem iron (FIG. 4). The corresponding residue in human haemoglobin beta is a redox-inactive phenylalanine. Thus the model predicts that human haemoglobin alpha subunit, but not the beta subunit, will possess the high affinity through-protein electron transfer pathway.

Example 3

The heterogeneous subunits of human haemoglobin exhibit different mechanisms of ferryl reduction.

Recombinant human haemoglobin was reacted with peroxide and the kinetics of ferryl haem reduction by ascorbate determined as described in example 1. The time course of ferryl haem reduction is not single exponential, as observed with myoglobin, but can be described using a double exponential function that generates two rate constants, one representing the observed rate constant for ferryl reduction of the alpha subunit and one representing the observed rate constant for ferryl reduction of the beta subunit. The kinetics of ferryl reduction (FIG. 5) shows that the subunits behave very differently towards reductants with only one of the haemoglobin subunits, assigned to the alpha subunit, exhibiting a high affinity electron transfer pathway.

Example 4

Site directed mutagenesis of α-Tyr42 eliminates the high affinity through-protein electron transfer pathway decreasing the rate of ferryl haem reduction.

Mutant variants of the alpha genes were created using site-directed mutagenesis. Primer sequences can be found in Table 5 (below). A high-fidelity enzyme, either Phusion™ (Finnzymes) or Pfu Ultra™ (Stratagene), was used according to the suppliers' specifications in the PCR reactions with the following PCR-program: 95° C. 2 min; 95° C. 30 s 55° C. 1 min 72° C. 5 min 16 cycles; 72° C. 10 min. The template DNA was then digested using Dpnl (Fermentas) and mutated plasmid transformed into Escherichia coli BL21 DE3 using standard procedures. Resulting clones were sequenced with BigDye™ terminator v.3.0 (Applied Biosystems) to confirm correct sequence.

Escherichia coli harbouring a plasmid encoding the modified alpha chains were grown and the modified alpha chains recovered using standard methods, essentially as described in Example 5 below.

Example 5

Site directed mutagenesis of Hb beta chain.

Using the methods described in example 4 above, a beta chain mutant of the human haemoglobin beta chain was made using the following primer pair to introduce a β-Phe41>Tyr mutation:

| Name | Sequence (5'-3') |
|---|---|
| bF41Y for | CCGTGGACCCAGCGTTACTTTGAATCCTTCGGTG (SEQ ID NO: 7) |
| bF41Y rev | CACCGAAGGATTCAAAGTAACGCTGGGTCCACGG (SEQ ID NO: 8) |

The genes for human haemoglobin alpha- and beta-chains were optimised for expression in Escherichia coli and cloned into the vector pETDuet resulting in HbpETDuet. Mutant variants of the alpha and beta genes were created using site-directed mutagenesis, as described above. A high-fidelity enzyme, either Phusion (Finnzymes) or Pfu Ultra (Stratagene), was used according to the suppliers' specifications in the PCR reactions with the following PCR-program: 95° C. 2 min; 95° C. 30 s 55° C. 1 min 72° C. 5 min 16 cycles; 72° C. 10 min. The template DNA was then digested using Dpnl (Fermentas) and mutated plasmid transformed into Escherichia coli BL21 DE3 using standard procedures. Resulting clones were sequenced with BigDye terminator v.3.0 (Applied Biosystems) to confirm correct sequence.

Escherichia coli BL21 DE3 harbouring the plasmid HbpETDuet was grown in 2 L flasks containing 1 L TB-medium with 100 μg/ml carbenicillin at 37° C. and 120 rpm until $OD_{620} \geq 1$. Expression of haemoglobin was then induced by adding 0.1 mM IPTG. Also 0.3 mM δ-aminolevulinic acid and CO-gas was added to improve protein yield. Culture conditions were altered after induction to 22° C. and 60 rpm. Cells were harvested and resuspended in 10 mM NaP buffer

TABLE 4

Primer sequences used for site-directed mutagenesis.

| Name | Sequence (5'-3') |
|---|---|
| aY42V for | CCTTCCCAACCACCAAAACCGTGTTCCCACACTTTGATCTG (SEQ ID NO: 3) |
| aY42V rev | CAGATCAAAGTGTGGGAACACGGTTTTGGTGGTTGGGAAGG (SEQ ID NO: 4) |
| aY42random for | CCTTCCCAACCACCAAAACCNNKTTCCCACACTTTGATCTG (SEQ ID NO: 5) |
| aY42random rev | CAGATCAAAGTGTGGGAAMNNGGTTTTGGTGGTTGGGAAGG (SEQ ID NO: 6) |

Recombinant human haemoglobin with α-Tyr42>Val (FIG. 6) or α-Tyr42>Trp (FIG. 7) mutation was reacted with peroxide and the kinetics of ferryl haem reduction by ascorbate determined as described in example 1. In both mutants the effect on the rate of ferryl reduction of the alpha subunit is dramatic with loss of the high affinity through-protein pathway as shown by the absence of the first hyperbola. Thus mutation of α-Tyr42 to a partially redox active tryptophan decreases the rate of ferryl reduction of the alpha subunit 2 fold at 10 μM ascorbate concentration and mutation of α-Tyr42 to a redox inactive valine decreases the rate of ferryl reduction of the alpha 12 fold at 10 μM ascorbate concentration.

pH 6.0 before sonication to break the cells. Haemoglobin was purified using ion-exchange chromatography with CM Sepharose FF (GE Healthcare). After the sample was applied to the column it was washed with 10 mM NaP buffer pH 6.0 until the absorbance returned to baseline. The haemoglobin was eluted with 70 mM NaP-buffer pH 7.2 and concentrated using VivaSpin columns (Vivascience). The concentrated sample was then applied to a Sephacryl S-200 gel filtration column (GE Healthcare) using elution-buffer. Haemoglobin containing fractions were concentrated as above and stored at −80° C. until needed.

Recombinant haemoglobin comprising the mutant alpha and beta chains was tested to demonstrate transfer of the high affinity electron transfer pathway from the alpha chain to the beta chain.

TABLE 1

Amino Acid Sequence and Helical Residue Notation for Human Haemoglobin A₀

| Helix | α | Helix | β |
|---|---|---|---|
| NA1 | 1 Val | NA1 | 1 Val |
| — | — | NA2 | 2 His |
| NA2 | 2 Leu | NA3 | 3 Leu |
| A1 | 3 Ser | A1 | 4 Thr |
| A2 | 4 Pro | A2 | 5 Pro |
| A3 | 5 Ala | A3 | 6 Glu |
| A4 | 6 Asp | A4 | 7 Glu |
| A5 | 7 Lys | A5 | 8 Lys |
| A6 | 8 Thr | A6 | 9 Ser |
| A7 | 9 Asn | A7 | 10 Ala |
| A8 | 10 Val | A8 | 11 Val |
| A9 | 11 Lys | A9 | 12 Thr |
| A10 | 12 Ala | A10 | 13 Ala |
| A11 | 13 Ala | A11 | 14 Leu |
| A12 | 14 Trp | A12 | 15 Trp |
| A13 | 15 Gly | A13 | 16 Gly |
| A14 | 16 Lys | A14 | 17 Lys |
| A15 | 17 Val | A15 | 18 Val |
| A16 | 18 Gly | — | — |
| AB1 | 19 Ala | — | — |
| B1 | 20 His | B1 | 19 Asn |
| B2 | 21 Ala | B2 | 20 Val |
| B3 | 22 Gly | B3 | 21 Asp |
| B4 | 23 Glu | B4 | 22 Val |
| B5 | 24 Tyr | B5 | 23 Val |
| B6 | 25 Gly | B6 | 24 Gly |
| B7 | 26 Ala | B7 | 25 Gly |
| B8 | 27 Glu | B8 | 26 Glu |
| B9 | 28 Ala | B9 | 27 Ala |
| B10 | 29 Leu | B10 | 28 Leu |
| B11 | 30 Glu | B11 | 29 Gly |
| B12 | 31 Arg | B12 | 30 Arg |
| B13 | 32 Met | B13 | 31 Leu |
| B14 | 33 Phe | B14 | 32 Leu |
| B15 | 34 Leu | B15 | 33 Val |
| B16 | 35 Ser | B16 | 34 Val |
| C1 | 36 Phe | C1 | 35 Tyr |
| C2 | 37 Pro | C2 | 36 Pro |
| C3 | 38 Thr | C3 | 37 Trp |
| C4 | 39 Thr | C4 | 38 Thr |
| C5 | 40 Lys | C5 | 39 Gln |
| C6 | 41 Thr | C6 | 40 Arg |
| C7 | 42 Tyr | C7 | 41 Phe |
| CE1 | 43 Phe | CD1 | 42 Phe |
| CE2 | 44 Pro | CD2 | 43 Glu |
| CE3 | 45 His | CD3 | 44 Ser |
| CE4 | 46 Phe | CD4 | 45 Phe |
| — | — | CD5 | 46 Gly |
| CE5 | 47 Asp | CD6 | 47 Asp |
| CE6 | 48 Leu | CD7 | 48 Leu |
| CE7 | 49 Ser | CD8 | 49 Ser |
| CE8 | 50 His | D1 | 50 Thr |
| — | — | D2 | 51 Pro |
| — | — | D3 | 52 Asp |
| — | — | D4 | 53 Ala |
| — | — | D5 | 54 Val |
| — | — | D6 | 55 Met |
| CE9 | 51 Gly | D7 | 56 Gly |
| E1 | 52 Ser | E1 | 57 Asn |
| E2 | 53 Ala | E2 | 58 Pro |
| E3 | 54 Gln | E3 | 59 Lys |
| E4 | 55 Val | E4 | 60 Val |
| E5 | 56 Lys | E5 | 61 Lys |
| E6 | 57 Gly | E6 | 62 Ala |
| E7 | 58 His | E7 | 63 His |
| E8 | 59 Gly | E8 | 64 Gly |
| E9 | 60 Lys | E9 | 65 Lys |
| E10 | 61 Lys | E10 | 66 Lys |
| E11 | 62 Val | E11 | 67 Val |
| E12 | 63 Ala | E12 | 68 Leu |
| E13 | 64 Asp | E13 | 69 Gly |
| E14 | 65 Ala | E14 | 70 Ala |
| E15 | 66 Leu | E15 | 71 Phe |
| E16 | 67 Thr | E16 | 72 Ser |
| E17 | 68 Asn | E17 | 73 Asp |
| E18 | 69 Ala | E18 | 74 Gly |
| E19 | 70 Val | E19 | 75 Leu |
| E20 | 71 Ala | E20 | 76 Ala |
| EF1 | 72 His | EF1 | 77 His |
| EF2 | 73 Val | EF2 | 78 Leu |
| EF3 | 74 Asp | EF3 | 79 Asp |
| EF4 | 75 Asp | EF4 | 80 Asn |
| EF5 | 76 Met | EF5 | 81 Leu |
| EF6 | 77 Pro | EF6 | 82 Lys |
| EF7 | 78 Asn | EF7 | 83 Gly |
| EF8 | 79 Ala | EF8 | 84 Thr |
| F1 | 80 Leu | F1 | 85 Phe |
| F2 | 81 Ser | F2 | 86 Ala |
| F3 | 82 Ala | F3 | 87 Thr |
| F4 | 83 Leu | F4 | 88 Leu |
| F5 | 84 Ser | F5 | 89 Ser |
| F6 | 85 Asp | F6 | 90 Glu |
| F7 | 86 Leu | F7 | 91 Leu |
| F8 | 87 His | F8 | 92 His |
| F9 | 88 Ala | F9 | 93 Cys |
| FG1 | 89 His | FG1 | 94 Asp |
| FG2 | 90 Lys | FG2 | 95 Lys |
| FG3 | 91 Leu | FG3 | 96 Leu |
| FG4 | 92 Arg | FG4 | 97 His |
| FG5 | 93 Val | FG5 | 98 Val |
| G1 | 94 Asp | G1 | 99 Asp |
| G2 | 95 Pro | G2 | 100 Pro |
| G3 | 96 Val | G3 | 101 Glu |
| G4 | 97 Asn | G4 | 102 Asn |
| G5 | 98 Phe | G5 | 103 Phe |
| G6 | 99 Lys | G6 | 104 Arg |
| G7 | 100 Leu | G7 | 105 Leu |
| G8 | 101 Leu | G8 | 106 Leu |
| G9 | 102 Ser | G9 | 107 Gly |
| G10 | 103 His | G10 | 108 Asn |
| G11 | 104 Cys | G11 | 109 Val |
| G12 | 105 Leu | G12 | 110 Leu |
| G13 | 106 Leu | G13 | 111 Val |
| G14 | 107 Val | G14 | 112 Cys |
| G15 | 108 Thr | G15 | 113 Val |
| G16 | 109 Leu | G16 | 114 Leu |
| G17 | 110 Ala | G17 | 115 Ala |
| G18 | 111 Ala | G18 | 116 His |
| G19 | 112 His | G19 | 117 His |
| GH1 | 113 Leu | GH1 | 118 Phe |
| GH2 | 114 Pro | GH2 | 119 Gly |
| GH3 | 115 Ala | GH3 | 120 Lys |
| GH4 | 116 Glu | GH4 | 121 Glu |
| GH5 | 117 Phe | GH5 | 122 Phe |
| H1 | 118 Thr | H1 | 123 Thr |
| H2 | 119 Pro | H2 | 124 Pro |
| H3 | 120 Ala | H3 | 125 Pro |
| H4 | 121 Val | H4 | 126 Val |
| H5 | 122 His | H5 | 127 Gln |
| H6 | 123 Ala | H6 | 128 Ala |
| H7 | 124 Ser | H7 | 129 Ala |
| H8 | 125 Leu | H8 | 130 Tyr |
| H9 | 126 Asp | H9 | 131 Gln |
| H10 | 127 Lys | H10 | 132 Lys |
| H11 | 128 Phe | H11 | 133 Val |
| H12 | 129 Leu | H12 | 134 Val |
| H13 | 130 Ala | H13 | 135 Ala |
| H14 | 131 Ser | H14 | 136 Gly |
| H15 | 132 Val | H15 | 137 Val |
| H16 | 133 Ser | H16 | 138 Ala |
| H17 | 134 Thr | H17 | 139 Asn |
| H18 | 135 Val | H18 | 140 Ala |
| H19 | 136 Leu | H19 | 141 Leu |
| H20 | 137 Thr | H20 | 142 Ala |
| H21 | 138 Ser | H21 | 143 His |
| HC1 | 139 Lys | HC1 | 144 Lys |
| HC2 | 140 Tyr | HC2 | 145 Tyr |
| HC3 | 141 Arg | HC3 | 146 His |

The invention claimed is:

1. A composition for use as a human blood substitute, wherein said composition a modified porphyrin-based oxygen-carrying protein and a reductant in a physiologically acceptable carrier, said protein in an unmodified state comprising a low affinity site of electron transfer between the reductant and a ferryl haem iron,
   wherein said modified protein comprises a modification to enhance or introduce a high affinity electron transfer pathway between the reductant and a ferryl haem iron via one or more amino acids,
   wherein
   said protein in an unmodified state is a member of the mammalian haemoglobin beta chain superfamily comprising Phe at the C7 position and the modified protein is a member of the mammalian haemoglobin beta chain superfamily, comprising a modification which is a Phe>Tyr substitution at the C7 position.

2. The composition of claim 1 wherein said protein in an unmodified state is a mammalian haemoglobin beta chain subunit comprising Phe at the C7 position and the modified protein is a mammalian haemoglobin beta chain subunit comprising a modification which is a Phe>Tyr substitution at the C7 position.

3. The composition of claim 1 wherein the modified protein is a human haemoglobin beta chain subunit or a member of the human haemoglobin beta chain superfamily.

4. The composition of claim 1 wherein the modified protein is a human beta, gamma or delta chain haemoglobin.

5. The composition of claim 1 wherein the modified protein is a human haemoglobin beta chain subunit wherein the modification is Phe41>Tyr.

6. The composition of claim 1 wherein the modified protein is present as a member of a dimer, tetramer or multimer.

7. The composition of claim 6 wherein the dimer, tetramer or multimer is cross-linked.

8. The composition of claim 1 wherein the modified protein is present in the form of a tetramer comprising two alpha globin subunits and two subunits of the modified protein.

9. The composition of claim 1 wherein the modified protein is in the form of a conjugated protein comprising the modified protein conjugated to a protecting group, wherein the protecting group is an anti-oxidant.

10. The composition of claim 1 wherein the modified protein is in the form of a conjugated protein comprising the modified protein conjugated to a protecting group, wherein the protecting group is a polyalkylene oxide.

* * * * *